United States Patent [19]

Yokoyama et al.

[11] Patent Number: 5,732,705
[45] Date of Patent: Mar. 31, 1998

[54] ULTRASOUND DIAGNOSTIC APPARATUS

[75] Inventors: Yukinobu Yokoyama; Ryoichi Kanda, both of Otawara, Japan

[73] Assignee: Kabushiki Kaisha Toshiba, Kawasaki, Japan

[21] Appl. No.: 711,782

[22] Filed: Sep. 10, 1996

[30] Foreign Application Priority Data

Sep. 12, 1995 [JP] Japan ................... 7-234075

[51] Int. Cl.$^6$ ...................... A61B 8/00
[52] U.S. Cl. .................. 128/660.07; 128/662.02
[58] Field of Search .................. 128/660.04, 660.05, 128/660.07, 660.08, 662.02; 364/413.25

[56] References Cited

U.S. PATENT DOCUMENTS

| | | | |
|---|---|---|---|
| 4,276,885 | 7/1981 | Tickner et al. | |
| 5,487,390 | 1/1996 | Cohen et al. | |
| 5,488,952 | 2/1996 | Schoolman | 128/660.07 |
| 5,513,640 | 5/1996 | Yamazaki et al. | 128/660.05 |

OTHER PUBLICATIONS

Rubin et al., "Power Doppler expands standard color capability", Diagnostic Imaging, pp. 66–69, Dec. 1993.

Primary Examiner—George Manuel
Attorney, Agent, or Firm—Finnegan, Henderson, Farabow, Garrett & Dunner, L.L.P.

[57] ABSTRACT

A region of interest of a subject is scanned with ultrasound to acquire echo signals. The echo signals are processed to obtain doppler signals. The doppler signals are processed to obtain color angio signals reflecting an amplitude of the doppler signals. The maximum value of levels of the color angio signals is increased from a first value to a second value by a contrast-enhancement effect. The level change within the first value is expressed by the brightness gradation. The level change the first value is expressed by the hue gradation. Therefore, the range less than the first value can be associated with the whole width of the usable brightness gradation of a color display, so that the level change less than the first value can be expressed with high contrast.

20 Claims, 5 Drawing Sheets

ULTRASOUND DIAGNOSTIC APPARATUS

BACKGROUND OF THE INVENTION

1. Field of the Invention

The present invention relates to an ultrasound diagnostic apparatus for enhancing the contrast of blood streams by use of contrast agents.

2. Description of the Related Art

Generally, ultrasound diagnostic apparatus have the following characteristics.

Specifically, as compared with the other imaging apparatus such as an X-ray diagnostic apparatus, an X-ray CT apparatus, an MRI, a nuclear medical diagnostic apparatus, etc., unfavorable influence, which is exerted upon a living body, is small. Moreover, real time performance is good, the size of the apparatus is small, and the manufacturing cost is low. These characteristics allow the ultrasound diagnosis to be used in the wide field including an examining for an embryo.

An MTI (moving target indicator) filter, which is generally used in the field of radar, was introduced into the ultrasound diagnostic apparatus, thereby making it possible to generate two-dimensional bloodstream data (including average velocity, dispersion, power) in real time. The average velocity denotes an average frequency of doppler signals, the dispersion means the dispersion of the frequency of the doppler signals, and the power shows intensity of the doppler signals.

In recent years, to improve a signal-to-noise (SIN) ratio and enhance visibility of a minute blood vessel or that of a low flow, there has been developed the so-called color angio technique in which power is added and averaged between frames.

FIG. 1 shows the conventional relationship between levels of color angio signals and displaying colors. As shown in FIG. 1, the color angio signals are included in a dynamic range of 20 dB. The level change of each of the color angio signals can be expressed by the change of brightness of a specific color (red). There was a problem in which contrast was little formed in the small amount of bloodstreams (★, ▲).

To solve the problem, contrast agents are injected into a subject. The difference between contrast agents and tissue in acoustic impedance is greatly larger than the difference between tissues in acoustic impedance. Due to this, intensity of echoes generated from the contrast agents is higher than that of echoes generated from the tissues. In accordance with increase in intensity of echoes, amplitude of the doppler signal is increased. Also, the color angio signals are increased. When contrast agents are injected into the blood vessel, the contrast between the blood vessel and the tissue is enhanced. In this case, contrast can be formed in the small amount of bloodstreams (★, ▲).

However, bloodstreams (●) which can been seen before being contrast-enhanced, exceeds 20 dB by contrast-enhancement effect as shown in FIG. 2. Then, the blood streams are all expressed by the brightest color, and no contrast was formed in the bloodstreams.

The above problem can be solved by corresponding 20 dB to intermediate brightness as shown in FIGS. 3 and 4. However, there occurs a problem in which the contrast before the contrast-enhancement is low, that is, only a half of brightness, which a display can provide, can be used.

SUMMARY OF THE INVENTION

An object of the present invention is to provide an ultrasound diagnostic apparatus which can express a level change of a signal with sufficiently high contrast both before and after contrast-enhancement.

According to a first aspect of the present invention, there is provided an ultrasound diagnostic apparatus for an examination using contrast agents having a contrast-enhancement effect, comprising:

scanning means for scanning a region of interest in a subject with ultrasound to acquire echo signals;

processing means for processing the echo signals to generate image signals, a maximum value of levels of the image signals is increased to a second value from a first value by the contrast-enhancement effect;

converting means for converting the image signals to color signals in accordance with a look-up table, the look-up table structured such that a level change within the first value is expressed by one of a brightness gradation and hues gradation and a level change over the first value is expressed by the other gradation; and displaying means for displaying the image of the region of interest based on the color signals.

According to a second aspect of the present invention, there is provided an ultrasound diagnostic apparatus for an examination using contrast agents having a contrast-enhancement effect, comprising:

scanning means for scanning a region of interest in a subject with ultrasound to acquire echo signals;

processing means for processing the echo signals to generate image signals, a maximum value of levels of the image signals is increased to a second value from a first value by the contrast-enhancement effect; and displaying means for gradating the image of the region of interest in accordance with first and second rules, the first rule being associated with a range less than the first value and the second rule being associated with a range more than the first value.

According to a third aspect of the present invention, there is provided an ultrasound diagnostic apparatus for an examination using contrast agents having a contrast-enhancement effect, comprising:

scanning means for scanning a region of interest in a subject with ultrasound to acquire echo signals;

processing means for processing the echo signals to generate image signals, a maximum value of levels of the image signals is increased to a second value from a first value by the contrast-enhancement effect;

converting means for converting the image signals to color signals in accordance with first and second rules, the first rule being associated with a first range less than the first value and the second rule being associated with a second range more than the first value; and displaying means for displaying the image of the region of interest based on the color signals.

According to a fourth aspect of the present invention, there is provided an ultrasound diagnostic apparatus for an examination using contrast agents having a contrast-enhancement effect, comprising:

scanning means for scanning a region of interest in a subject with ultrasound to acquire echo signals;

processing means for processing the echo signals to generate image signals, a dynamic range of levels of the image signals being enlarged from a first dynamic range to a second dynamic range by the contrast-enhancement effect; and displaying means for displaying an image of the region of interest in accordance with first and second gradating rules, the first gradating rule being associated with the first dynamic range and the second rule being associated with a third range over the first dynamic range and in the second dynamic range.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

DETAILED DESCRIPTION OF THE PREFERRED EMBODIMENT

An embodiment of the present invention will be explained with reference to the drawings.

Figure 5:
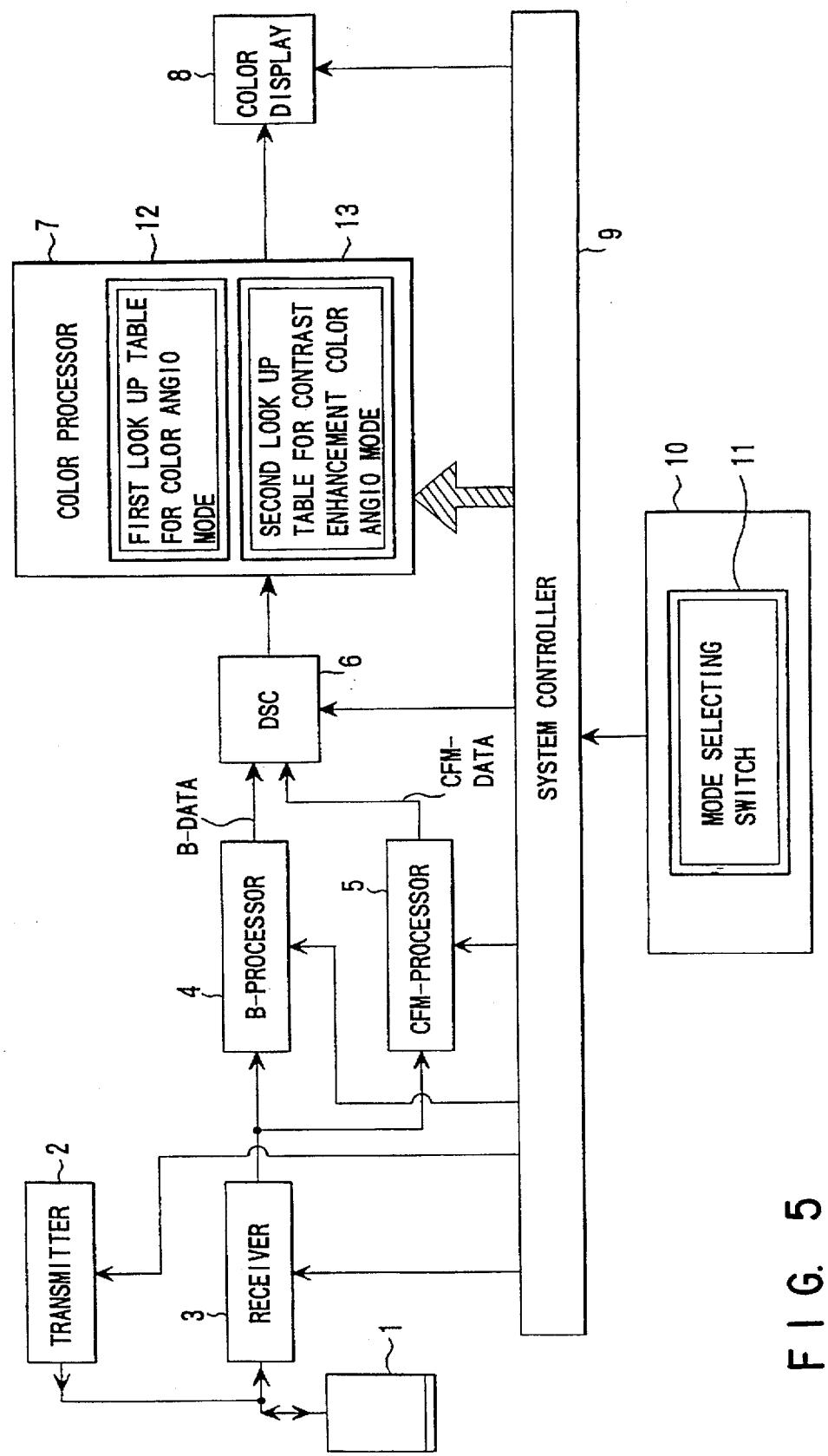
FIG. 5 is a block diagram showing an ultrasound diagnostic apparatus of one embodiment of the present invention.

FIG. 5 shows the structure of the ultrasound diagnostic apparatus of the embodiment of the present invention. In the figure, a system controller 9 is a main controller for an entire apparatus. A console 10 is connected to the system controller 9. A mode selecting switch 11 is provided to the console 10. An operator can select an arbitrary mode from a plurality of modes by operating the switch 11. The plurality of modes includes a color angio mode and a contrast-enhancement color angio mode. The color angio mode is selected when contrast agents are not used. The contrast-enhancement color angio mode is selected when contrast agents are used.

A probe 1 has piezoelectric elements for converting an electrical signal to an ultrasound wave and the ultrasound wave to the electrical signal.

A transmitter 2 comprises a clock generator, a rate pulse generator, delay circuits, and pulsers. The clock generator generates a clock pulse. The rate pulse generator divides the clock pulse, and generates a rate pulse of, e.g., 5 kHz. The rate pulse is distributed to a plurality of pulsers. The rate pulses are individually delayed by the delay circuits so as to be sent to the plurality of pulsers, respectively. If the pulsers receive the rate pulses, the pulsers apply voltage pulses each having a high frequency to the piezoelectric elements, respectively.

Thereby, the ultrasonic pulses are transmitted to the subject from the probe 1. A part of the ultrasound waves are reflected at a boundary of the acoustic impedance to be directed to the probe 1 as an echo. The remaining ultrasound wave are passed through the boundary. The echoes are converted to electric signals by the piezoelectric elements of the probe 1.

A receiver 3 comprises preamplifiers, delay circuits, and an adder. The preamplifiers individually amplify the signals sent from the piezoelectric elements of the probe 1. The amplified signals are individually delayed by the delay circuits to be added to each other by the adder. Such transmitting and receiving is periodically repeated. In a case of a sector scanning, the delay times are switched, so that a region of interest is scanned by the ultrasound waves. In a case of a linear scanning, the groups of driving elements are switched, so that the region of interest is scanned by the ultrasound waves. Thereby, the echo signals of the region of interest are acquired. Such scannings are periodically repeated.

A B-mode processor 4 detects envelopes of the echo signals sent from the receiver 3 to produce B-mode image signals. The B-mode image signals are sent to a digital scanning converter (DSC) 6.

A CFM mode processor 5 comprises an orthogonal phase detector, an A/D converter, an MTI filter, an auto-correlator, a doppler calculator, and a color angio calculator. The orthogonal phase detector orthogonally phase-detects the echo signals sent from the receiver 3 to obtain doppler signals doppler-shifted by moving materials such as bloodstreams.

The doppler signals are sent to the MTI filter through the A/D converter. The MTI filter removes clatter components (low frequencies) from the doppler signals so as to extract bloodstream components (high frequencies).

The auto-correlator frequency-analyzes the bloodstream components in real time. The doppler calculator calculates two-dimensional bloodstream data based on the result of the analysis. Bloodstream data includes average velocity data, dispersion data, and power data. Average velocity data (average velocity signals) is calculated as average frequencies of the doppler signals. Dispersion data (dispersion signals) is calculated as dispersions of the frequencies of the doppler signals. Power data (power signals) is calculated as a square of amplitude of the doppler signals. For obtaining color angio signals, the color angio calculator adds and averages the power signals between the frames. The levels of the power signals and those of the color angio signals reflect the amount of bloodstreams. The average velocity signals, the dispersion signals, the power signals, and the color angio signals are sent to the digital scanning converter 6.

An operator designates one kind of signals or two kinds of signals from the B-mode signals, the average velocity signals, the dispersion signals, the power signals, the color angio signals. Through the digital scanning converter 6, the designated signals are combined in one frame so as to be output as image signals. The following will explain the case of the color angio signals.

A color processor 7 has a plurality of look-up tables and allocates color signals (for example, RGB signals) to the color angio signals according to the selected one of the tables. In this case, the color signals are allocated in accordance with the level of color angio signals supplied from the digital scanning converter 6.

The plurality of look-up tables includes a first look-up table 12 for a color angio mode and a second look-up table 13 for a contrast-enhancement color angio mode. If the color angio mode is selected, the first look-up table 12 is used. If the color angio mode is selected, the second look-up table 13 is used.

A color display 8 displays a color angio image of the region of interest in accordance with the color signals sent from the color processor 7.

The following will explain the first and second look-up tables 12 and 13. In this case, it is assumed that a gain of a preamplifier, which is obtained when the color angio mode is selected, is the same as that of the amplifier, which is obtained when the contrast-enhancement color angio mode is selected. When this gain is changed, the system dynamic range is enlarged or reduced. In this case, it is assumed that the dynamic range is "20 dB". And the dynamic range is enlarged due to the contrast-enhancement effect. The level of the enlargement corresponds to a kind of contrast agents, therefore we can understand the enlarged dynamic range based on the kind of selected contrast agents beforehand. In this case, it is assumed that the enlarged dynamic range is "40 dB".

First, a contrast-enhancement effect will be explained. The contrast agents, for example, minute bubbles, are injected into the blood vessel of the subject. The difference between the contrast agents and the tissue in acoustic impedance is greatly larger than the difference between the tissues in acoustic impedance. Thus, intensity of the echo reflected at the boundary between the contrast agents and the tissue is greater than that of the echo reflected at the boundary between the tissues. The amplitude of the doppler signal reflects the intensity of the echo, i.e. the size of the bloodstreams. Since the color angio signals are calculated as a square of amplitude of the doppler signal, the levels of the color angio signals are increased by the contrast-enhancement effect.

The levels of the color angio signals, which are acquired before the contrast agents reaches the region of interest, are included in a predetermined first dynamic range (0 dB to 20 dB). A minimum value of the first dynamic range is expressed by $L_{min\text{-}before}$ and a maximum value is expressed by $L_{max\text{-}before}$.

The levels of the color angio signals, which are acquired after the contrast agents reaches the region of interest, are included in a second dynamic range (0 dB to 40 dB). A minimum value of the third dynamic range (20 dB to 40 dB) over the first dynamic range and in the second dynamic range is expressed by $L_{min\text{-}after}$ and a maximum value is expressed by $L_{max\text{-}after}$.

The dynamic range of the color angio signals is enlarged to the second dynamic range from the first dynamic range by the contrast-enhancement effect. The maximum value of the levels of the color angio signals is increased from $L_{max\text{-}before}$ (first value) to $L_{max\text{-}after}$ (second value).

Figure 1:
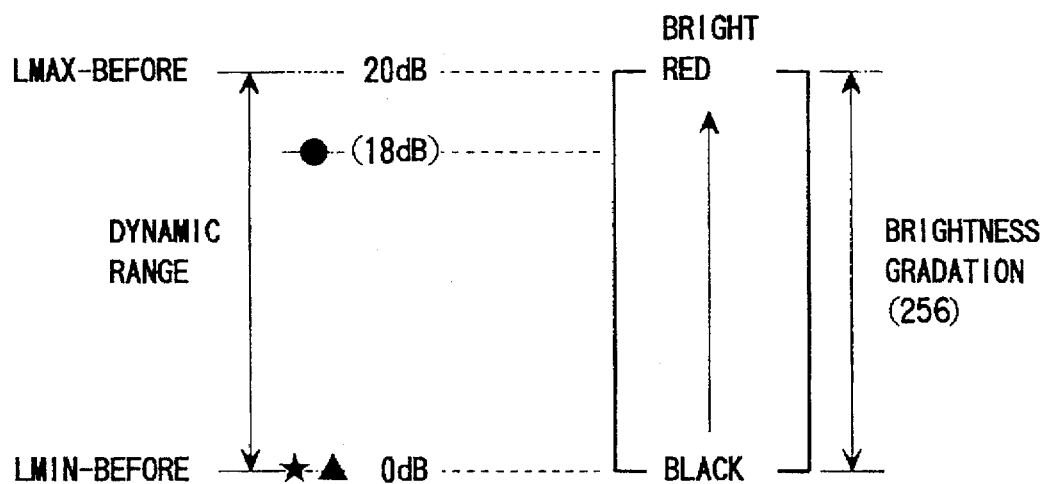
FIG. 1 is a view showing the conventional relationship between a level of a color angio signal and a displaying color in a state that no contrast-enhancement effect is exerted.
Figure 2:
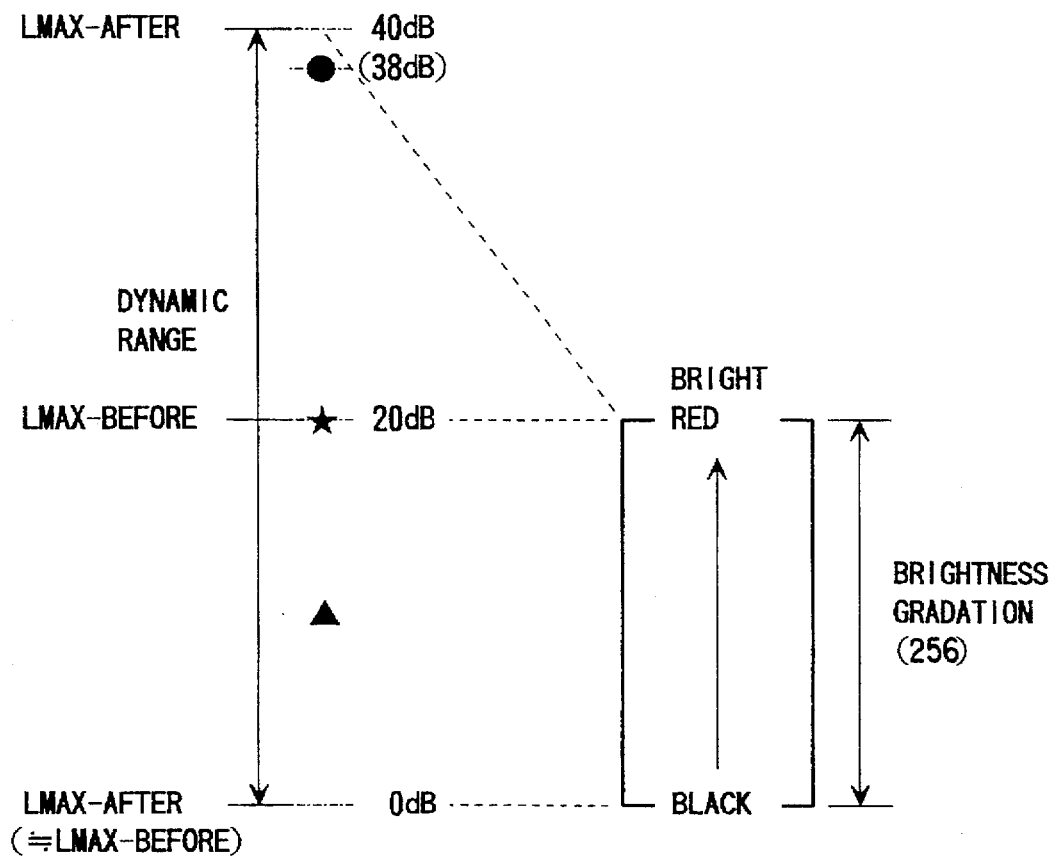
FIG. 2 is a view showing the conventional relationship between a level of a color angio signal and a displaying color in a state that a contrast-enhancement effect is exerted.
Figure 3:
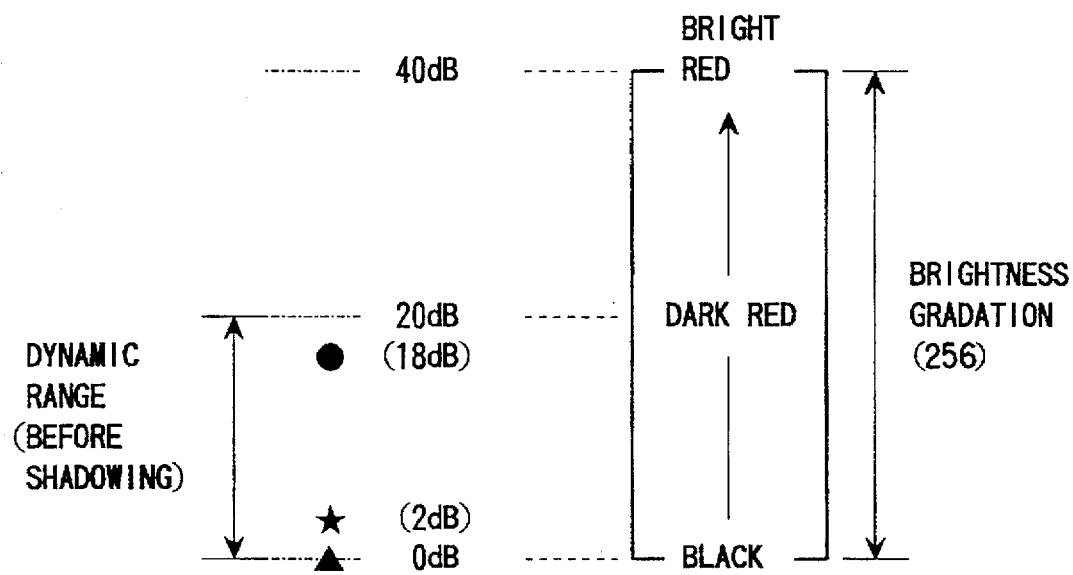
FIG. 3 is a view showing the other conventional relationship between a level of a color angio signal and a displaying color in a state that no contrast-enhancement effect is exerted.
Figure 4:
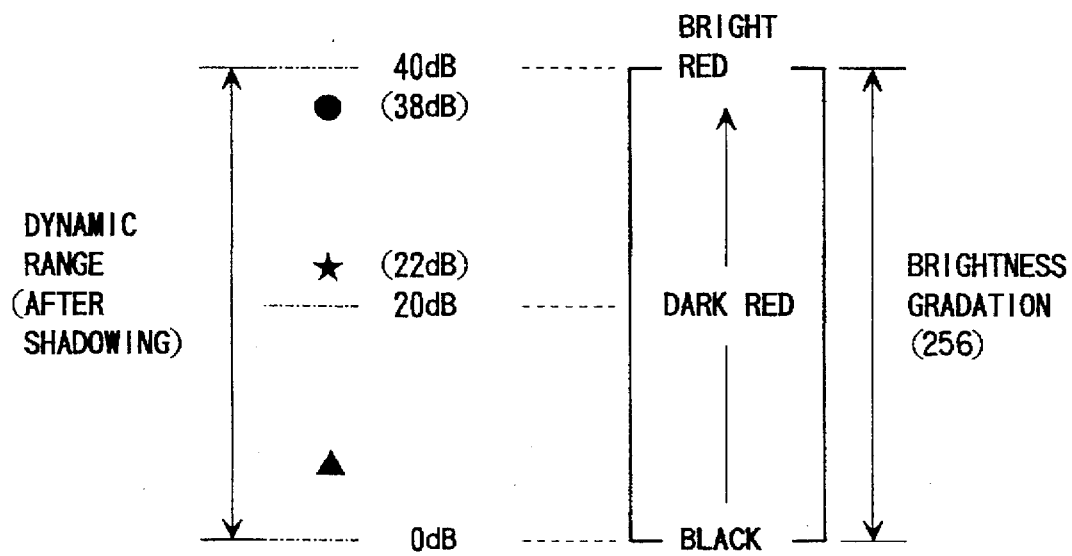
FIG. 4 is a view showing the other conventional relationship between a level of a color angio signal and a displaying color in a state that a contrast-enhancement effect is exerted.

As shown in FIGS. 1 and 2, the first look-up table 12 is structured such that the change of the levels of the color angio signals is gradated by brightness of a specific color (red). The maximum value $L_{max\text{-}before}$ of the color angio signals corresponds to the red, is the brightest color, which the color display 8 can display. The minimum value $L_{min\text{-}before}$ of the color angio signals corresponds to the black, which is the darkest color.

Figure 6:
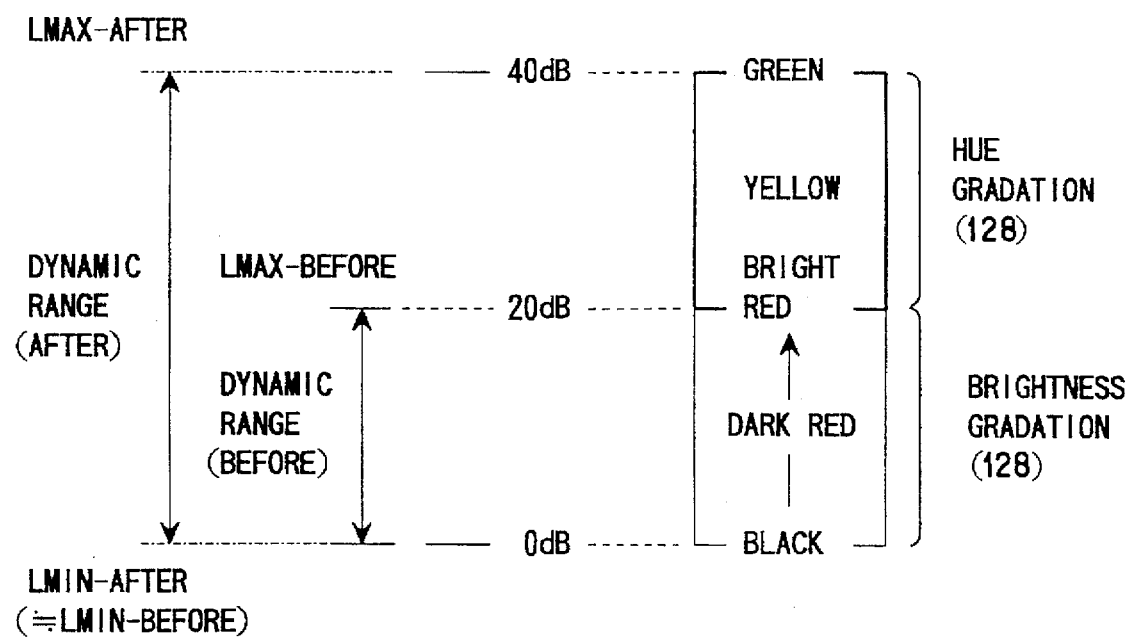
FIG. 6 is a view showing the conventional relationship between levels of color angio signals and displaying colors based on a second look-up table of FIG. 5.

As shown in FIG. 6, the second look-up table 13 is structured such that the first dynamic range (0 dB to 20 dB) and the third dynamic range (20 dB to 40 dB) are different from each other in a rule for allocating the gradation to the signal levels.

In other words, in the second look-up table 13, the change of the signal levels included in the first dynamic range is expressed by the brightness gradation with the specific color (red). The change of the signal levels included in the third dynamic range is expressed by the hues gradation.

Moreover, the first dynamic range corresponds to the usable maximum gradation width of the display 8, the $L_{max\text{-}before}$ ($L_{min\text{-}after}$) is the brightest color, which the color display 8 can display. In other words, the maximum value $L_{max\text{-}before}$ of the color angio signals, which are acquired before the contrast agents reaches the region of interest, is set to correspond to the brightest color, which the color display 8 can display. Thereby, sufficient contrast can be obtained at the time when the contrast agents reach the region of interest.

The color corresponding to the minimum value $L_{min\text{-}after}$ of the third dynamic range conforms to the brightest color, red, corresponding to the maximum $L_{max\text{-}before}$ of the first dynamic range. Thereby, the hue gradation is smoothly formed in the vicinity of the boundary between the first and third dynamic ranges without being abruptly changed.

Figure 7:
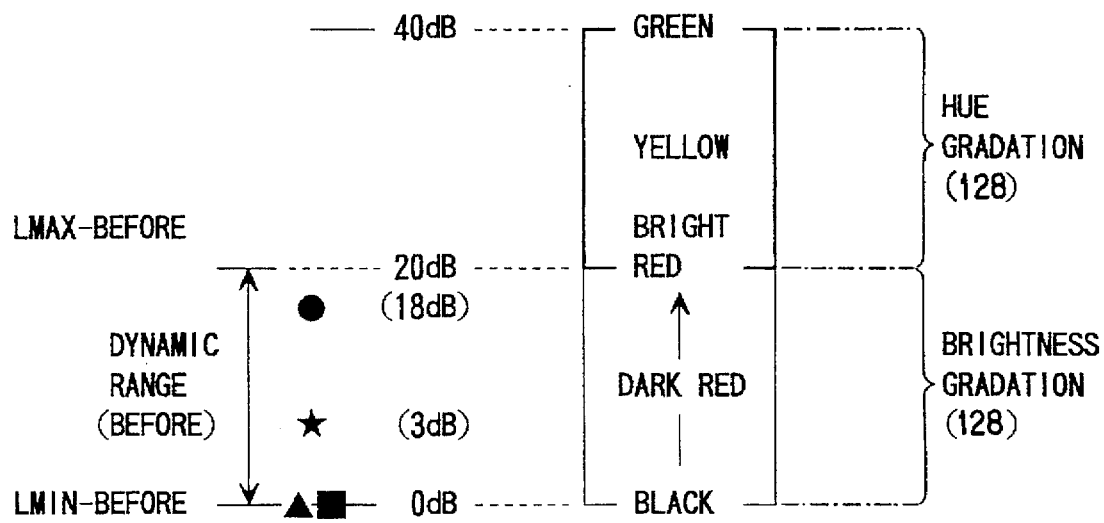
FIG. 7 is a view showing the relationship between levels of color angio signals and displaying colors in a state that no contrast-enhancement effect is exerted based on a second look-up table of FIG. 5.
Figure 8:
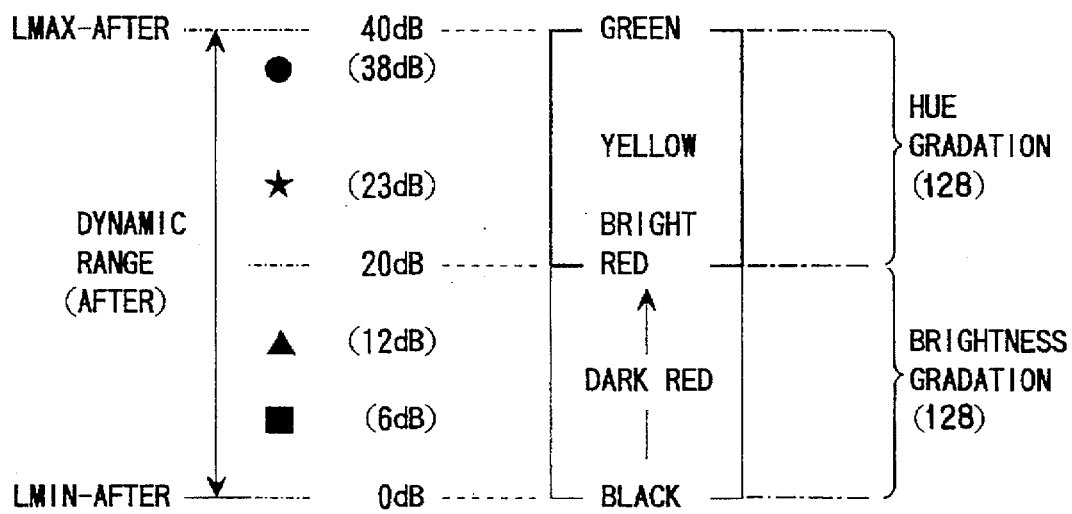
FIG. 8 is a view showing the relationship between levels of color angio signals and displaying colors in a state that a contrast-enhancement effect is exerted based on a second look-up table of FIG. 5.

FIG. 7 shows the relationship between the levels of the color angio signals and displaying colors before the contrast agent reaches the region of interest. FIG. 8 shows the relationship between the levels of the color angio signals and displaying colors after the contrast agent reaches the region of interest. No contrast-enhancement effect is exerted before the contrast agent reaches the region of interest. At this time, the dynamic range (first dynamic range) of the color angio signals is 20 dB, and the change of the levels can be expressed by the brightness of the specific color (red).

Before the contrast agent reaches the region of interest, contrast is larger in the relatively large bloodstreams (●, ★), and contrast is small in the relatively small bloodstreams (▲, ■).

If the contrast agent reaches the region of interest, the contrast-enhancement effect is exerted, and the levels of the color angio signals are increased, and the dynamic range is enlarged to 40 dB. Then, contrast is increased in the relatively small bloodstreams (▲, ★) by the contrast-enhancement effect. The contrast in the relatively large bloodstreams (●, ★) is expressed by the hue gradation in place of the brightness gradation.

As explained above, the change of the levels in the first dynamic range can be expressed by the brighten gradation. Then, the change of the levels in the third dynamic range, (20 dB to 40 dB), can be expressed by the hue gradation.

Therefore, according to the embodiment of the present invention, before contrast-enhancement, sufficient contrast can be obtained by use of the whole width of the brightness, which the color display 8 can display. Then, even after contrast-enhancement, sufficient contrast can be obtained by use of the change of brightness and that of the hues. Moreover, there can be obtained an advantage in which no adjustment of the dynamic range is needed before and after contrast-enhancement.

The present invention can be variously modified without being limited to the above-explained embodiment. In the above explanation, the change of the signal levels was expressed by the change of brightness in the range of 20 dB or less, and expressed by the change of the hues in the range of 20 dB or more. However, the change of the signal levels may expressed by the change of the hues in the range of 20 dB or less, and expressed by the change of brightness in the range of 20 dB or more. Moreover, the change of the signal levels may be expressed by the combination of the change of brightness and that of the hues in both ranges of 20 dB or less and more so as to change the hues in both ranges of 20 dB or less and more. The present invention can be applied to the signal, which reflects amplitude of the echo signal such as a B-mode signal, a color signal, etc.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasound diagnostic apparatus for an examination using contrast agents having a contrast-enhancement effect, comprising:

scanning means for scanning a region of interest in a subject with ultrasound to acquire echo signals;

processing means for processing the echo signals to generate image signals, a maximum value of levels of the image signals is increased to a second value from a first value by the contrast-enhancement effect;

converting means for converting the image signals to color signals in accordance with a look-up table, the look-up table structured such that a level change within the first value is expressed by one of a brightness gradation and hue gradation, and a level change over the first value is expressed by the other gradation; and displaying means for displaying the image of said region of interest based on the color signals.

2. The apparatus according to claim 1, wherein said processing means extracts doppler signals of bloodstreams from said echo signals and obtains a power of the doppler signals from the image signals.

3. The apparatus according to claim 2, wherein said processing means adds and averages the power of the doppler signals between frames.

4. The apparatus according to claim 1, wherein said look-up table is structured such that the level change within the first value is expressed by the brightness gradation and the level change over the first value is expressed by the hue gradation.

5. The apparatus according to claim 4, wherein said first value is expressed by the maximum brightness.

6. An ultrasound diagnostic apparatus for an examination using contrast agents having a contrast-enhancement effect, comprising:

scanning means for scanning a region of interest in a subject with ultrasound to acquire echo signals;

processing means for processing the echo signals to generate image signals, a maximum value of levels of the image signals is increased to a second value from a first value by said contrast-enhancement effect; and displaying means for gradating the image of the region of interest in accordance with first and second rules, the first rule being associated with a range less than the first value and the second rule being associated with a range more than the first value.

7. The apparatus according to claim 6, wherein said processing means extracts doppler signals of bloodstreams from said echo signals and obtains a power of the doppler signals from the image signals.

8. The apparatus according to claim 7, wherein said processing means adds and averages the power of the doppler signals between frames.

9. The apparatus according to claim 6, wherein the level change within the first value is expressed by the brightness gradation by the first rule, and the level change over the first value is expressed by the hues gradation by the second rule.

10. The apparatus according to claim 9, wherein the first value is expressed by a maximum value of brightness.

11. An ultrasound diagnostic apparatus for an examination using contrast agents having a contrast-enhancement effect, comprising:

scanning means for scanning a region of interest in a subject with ultrasound to acquire echo signals;

processing means for processing said echo signals to generate image signals, a maximum value of levels of the image signals is increased to a second value from a first value by the contrast-enhancement effect;

converting means for converting the image signals to color signals in accordance with first and second rules, the first rule being associated with a first range less than the first value and the second rule being associated with a second range more than the first value; and displaying means for displaying the image of the region of interest based on the color signals.

12. The apparatus according to claim 11, wherein said processing means extracts doppler signals of bloodstreams from said echo signals and obtains a power of the doppler signals from the image signals.

13. The apparatus according to claim 12, wherein said processing means adds and averages the power of the doppler signals between frames.

14. The apparatus according to claim 11, wherein the level change within the first range is expressed by the brightness gradation by the first rule, and the level change within the second range is expressed by the hue gradation by the second rule.

15. The apparatus according to claim 14, wherein the first value is expressed by a maximum value of brightness.

16. An ultrasound diagnostic apparatus for an examination using contrast agents having a contrast-enhancement effect, comprising:

scanning means for scanning a region of interest in a subject with ultrasound to acquire echo signals;

processing means for processing the echo signals to generate image signals, a dynamic range of levels of the image signals being enlarged from a first dynamic range to a second dynamic range by the contrast-enhancement effect; and displaying means for displaying an image of the region of interest in accordance with first and second gradating rules, the first gradating rule being associated with the first dynamic range and the second rule being associated with a third range over the first dynamic range and in the second dynamic range.

17. The apparatus according to claim 16, wherein said processing means extracts doppler signals of bloodstreams from said echo signals and obtains a power of the doppler signals from the image signals.

18. The apparatus according to claim 17, wherein said processing means adds and averages the power of the doppler signals between frames.

19. The apparatus according to claim 16, wherein the level change in the first dynamic range is expressed by the brightness gradation by the first rule, and the level change in the third range is expressed by the hue gradation by the second rule.

20. The apparatus according to claim 16, wherein the first value is expressed by a maximum value of brightness.

* * * * *